United States Patent [19]

Conkling et al.

[11] Patent Number: 5,002,541
[45] Date of Patent: Mar. 26, 1991

[54] METHOD AND DEVICE FOR REMOVING AND COLLECTING URINE

[75] Inventors: J. Michael Conkling, Pretty Prairie; Glen W. Ediger, Newton; Gary P. Israel; Richard E. Ten Eyck, both of Wichita, all of Kans.

[73] Assignee: Martin and Associates, Inc., Wichita, Kans.

[21] Appl. No.: 945,844

[22] Filed: Dec. 22, 1986

Related U.S. Application Data

[63] Continuation-in-part of Ser. No. 622,117, Jun. 19, 1984, Pat. No. 4,631,061.

[51] Int. Cl.⁵ .............................................. A61M 1/00
[52] U.S. Cl. .................................... 604/319; 604/349; 604/324; 604/329
[58] Field of Search ............... 604/317, 318, 319, 320, 604/321, 322, 323, 324, 325, 326, 327, 328, 329, 330, 331, 349; 128/138 A, 760, 761, 765, 766; 4/301, 313, 314, 316, 144.1, 144.2, 144.3, 144.4, DIG. 3

[56] References Cited

U.S. PATENT DOCUMENTS

| | | | |
|---|---|---|---|
| 3,349,768 | 10/1967 | Keane | 128/276 |
| 3,964,111 | 6/1976 | Packer | 4/110 |
| 4,023,216 | 5/1977 | Li | 4/110 |
| 4,117,845 | 10/1978 | Brown | 128/295 |
| 4,198,979 | 4/1980 | Cooney et al. | 604/329 |
| 4,212,295 | 7/1980 | Snyder | 128/138 A |
| 4,270,231 | 6/1981 | Zint | 4/144.1 |
| 4,345,341 | 8/1982 | Saito | 4/301 |
| 4,345,342 | 8/1982 | Saito | 4/301 |
| 4,360,933 | 11/1982 | Kimura et al. | 4/301 |
| 4,484,917 | 11/1984 | Blackmon | 604/329 |
| 4,505,703 | 3/1985 | Gale et al. | 604/317 |
| 4,528,703 | 7/1985 | Kraus | 4/144 |
| 4,531,939 | 7/1985 | Izumi | 604/317 X |
| 4,610,675 | 9/1986 | Triunfol | 604/329 |

FOREIGN PATENT DOCUMENTS

| | | | |
|---|---|---|---|
| 794640 | 9/1968 | Canada | 604/329 |
| 1193261 | 5/1970 | United Kingdom | 604/329 |
| 2107190 | 4/1983 | United Kingdom | 604/329 |

Primary Examiner—Nam X. Nguyen
Attorney, Agent, or Firm—Gary M. Polumbus

[57] ABSTRACT

A device for detecting the presence of urine at the genital region of an individual and removing and storing the urine. The device includes an external urine collecting vessel which is supported at the genital region to contain the urine within the vessel. Liquid sensors are contained within the vessel for detecting the presence of urine and automatically activating a pump to draw the urine through a tubing to a temporary storage chamber. A liquid impermeable liner is place within the collecting vessel for improved hygiene and for directing the urine away from the individual.

7 Claims, 4 Drawing Sheets

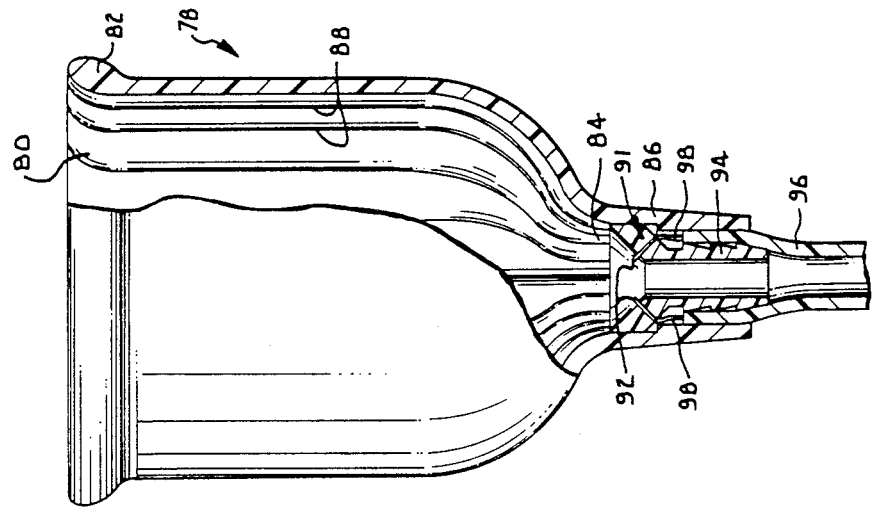
Fig. 8.
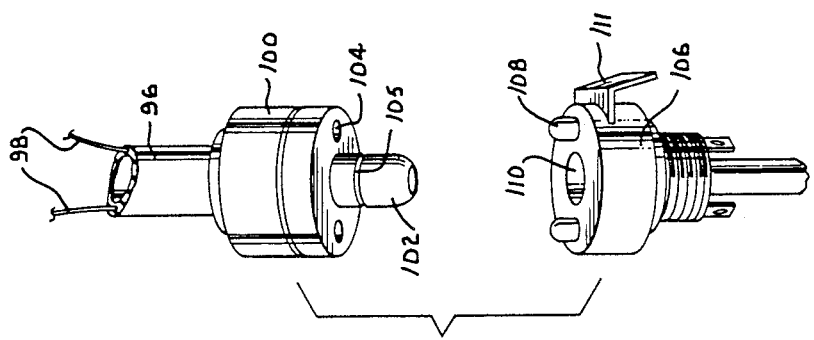
Fig. 7.
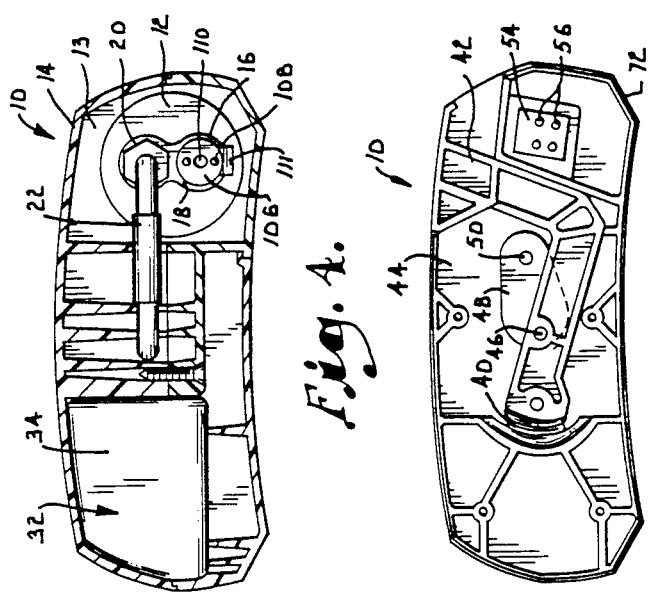
Fig. 4.
Fig. 5.
Fig. 6.

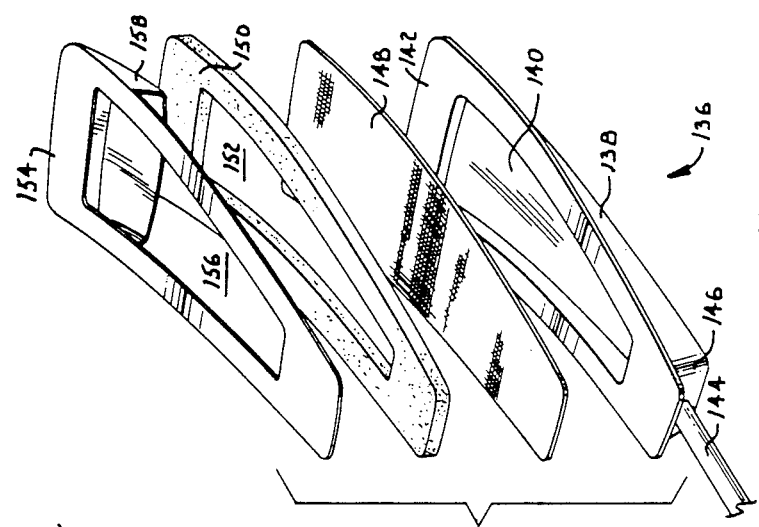
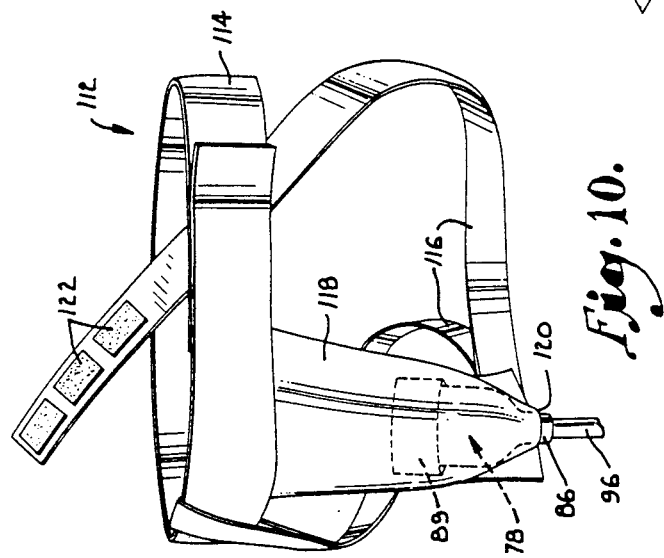
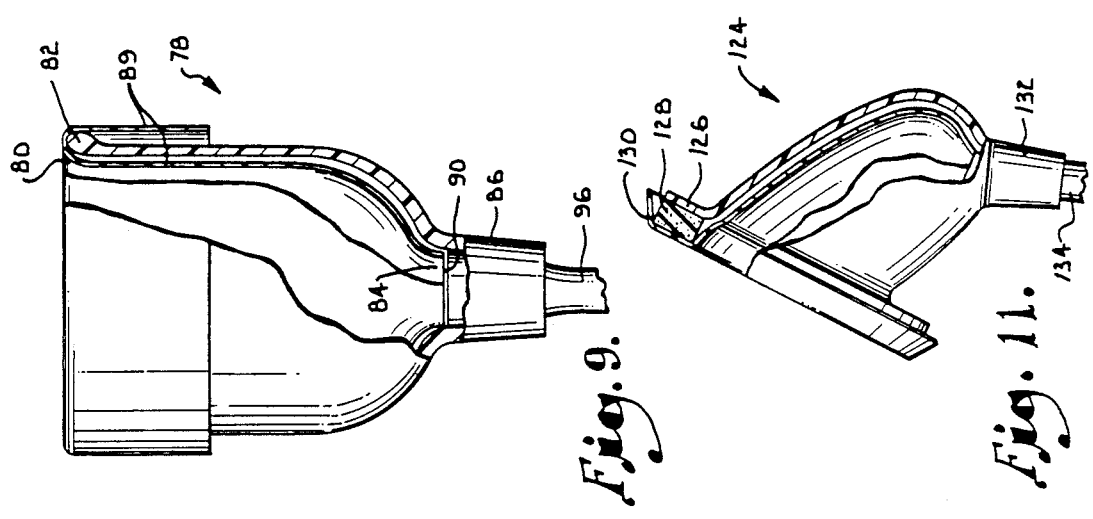

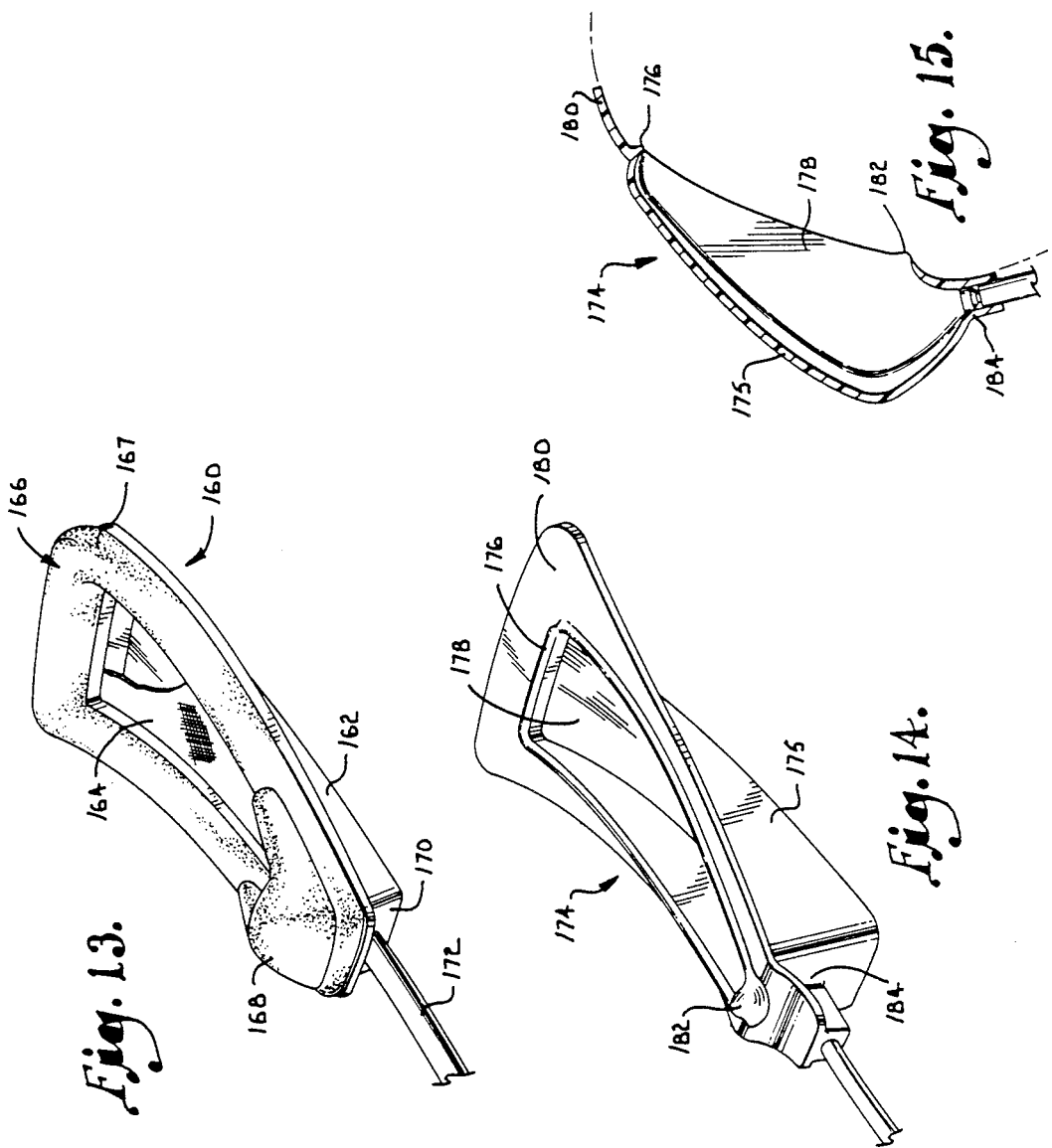

METHOD AND DEVICE FOR REMOVING AND COLLECTING URINE

This application is a continuation-in-part of copending U.S. application Ser. No. 622,117 filed June 19, 1984 and entitled "Automatic Urine Detecting, Collecting and Storage Device" now U.S. Pat. No. 4,631,061.

BACKGROUND OF THE INVENTION

This invention relates to devices for use by individuals who are unable to control the flow of urine and, more particularly, to a device for detecting the presence of urine, and subsequently removing and storing the urine.

Millions of individuals are afflicted with urinary problems of varying severity, ranging from those individuals who have no control over their bladder function to those individuals who on occasion are unable to reach an appropriate location for urination. Failure to control the flow of urine is a source of acute embarrassment and frequently requires that otherwise healthy individuals adopt a life of relative seclusion. Incontinence also creates serious health risks for bedridden individuals such as the aged and severely ill and hospitals and nursing facilities spend enormous amounts of time, money, and material dealing with the effects of incontinence.

Previous attempts at solving the incontinence problem in males have focused on urethetic catheters and condom-like sheaths. The catheter must be internally inserted and poses a serious risk of urinary tract infection in addition to the extreme discomfort it may create. The sheath device is worn externally and results in discomfort because it is in direct contact with the skin of the patient and also creates a high risk of infection. These device are frequently intentionally or inadvertantly displaced by the patient because of the discomfort created and require that the patient be restrained to prevent displacement of the device.

Both the catheter and sheath devices rely on gravity to remove the urine to a temporary storage container and failure to maintain the container at a lower elevation than the device prevents the proper removal of the urine. Devices have been developed which provide a vacuum to remove the urine to a storage container, but require that the individual be sufficiently alert to properly position the urine collecting device when needed. These devices are of limited benefit to patients who experience incontinence problems while asleep or who have restricted physical movement and are unable to position the device.

Incontinence devices for females have been limited to internal catheter devices which suffer from the same shortcomings as the male catheter devices. There are no satisfactory external devices for use by females.

While the presently known male and female incontinence devices may prove to be adequate for specific and limited applications, they fail to provide an acceptable solution to the incontinence problem.

SUMMARY OF THE INVENTION

It is an object of this invention to provide a device for use by male and female individuals unable to control the flow of urine which will detect the presence of urine and remove and temporarily store the urine until it may be disposed of in a suitable receptacle.

As a corollary to the previous object, it is another object of this invention to provide a device as described which is portable to allow mobility of incontinent individuals.

It is a further object of this invention to provide a device for use by incontinent individuals which automatically detects the flow of urine and removes and stores the urine so that the device may be utilized by individuals while asleep or by those individuals with restricted physical movement.

It is yet further object of this invention to provide a urine sensing, removal and storage device for use by incontinent individuals which utilizes a urine collector compatible with but detached from the genital area of the individuals for improved hygiene and comfort.

As a corollary to the previous objective, it is an object of this invention to provide a device for use by incontinent individuals which utilizes a sanitary disposable liner to separate the urine collector from direct contact with the skin of the individual to ensure proper hygiene.

It is a still further object of this invention to provide a device for detecting the presence of and removing and storing urine which utilizes urine collecting vessels which may be maintained in proximity to the genital area of an individual and may be concealed under the clothing of the individual.

It is also an object of this invention to provide a device for the detection, removal and storage of urine which may be used by males and females whether they are in an upright, sitting or prone position.

To accomplish these and other objects of the invention which will be readily apparent to those of skill in the art, a collecting vessel shaped to conform to the genital region of an individual is coupled with a device comprising pump means and storage means. Liquid sensing means may be provided in the collecting vessel for detecting the presence of urine to cause activation of the collecting means to remove urine from the collecting vessel. The vessel may include a disposable liner to direct the urine away from the individual and to separate the individual from contact with the vessel.

BRIEF DESCRIPTION OF THE DRAWINGS

In the accompanying drawings which form a part of the specification and are to be read in conjunction therewith and in which like reference numerals are used to indicate like parts in the various views:

FIG. 4 is a sectional view of the collecting and storage device taken along line 4—4 of FIG. 1 and showing details of construction.

FIG. 5 is a sectional view of the collecting and storage device taken along line 5—5 of FIG. 1 and showing a pinch lever in a closed position.

FIG. 6 is a sectional view similar to FIG. 5 with the pinch lever in a released position.

FIG. 7 is an enlarged exploded perspective view of connecting plugs used to couple a urine collecting vessel to the collecting and storage device.

FIG. 8 is a enlarged side elevational view of a male urine collecting vessel coupled with a flow line and with portions broken away to show liquid sensors and other internal details.

FIG. 9 is a side elevational view of the male urine collecting vessel shown in FIG. 8 and shown on a reduced scale and with portions broken away to show a liner positioned within the vessel.

FIG. 10 is a perspective view of a garmet which may be used to maintain the vessel of FIGS. 8 and 9 shown in broken lines in position on a male.

FIG. 11 is side elevational view of an alternate embodiment of a male urine collecting vessel with portions broken away to show details of construction.

FIG. 12 is an exploded perspective view of a female urine collecting vessel.

FIG. 13 is a perspective view of an alternate embodiment of a female urine collecting vessel.

FIG. 14 is a perspective view of another embodiment of a female urine collecting vessel.

FIG. 15 is a side sectional view of the female urine vessel of FIG. 14 shown in a user position.

DESCRIPTION OF THE PREFERRED EMBODIMENTS

Figure 3:
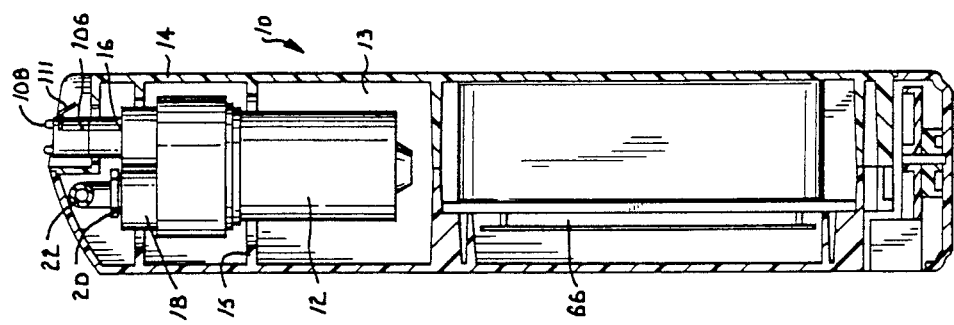
FIG. 3 is a side sectional view of the collecting and storage device taken along line 3—3 of FIG. 1 with the charging stand removed.
Figure 2:
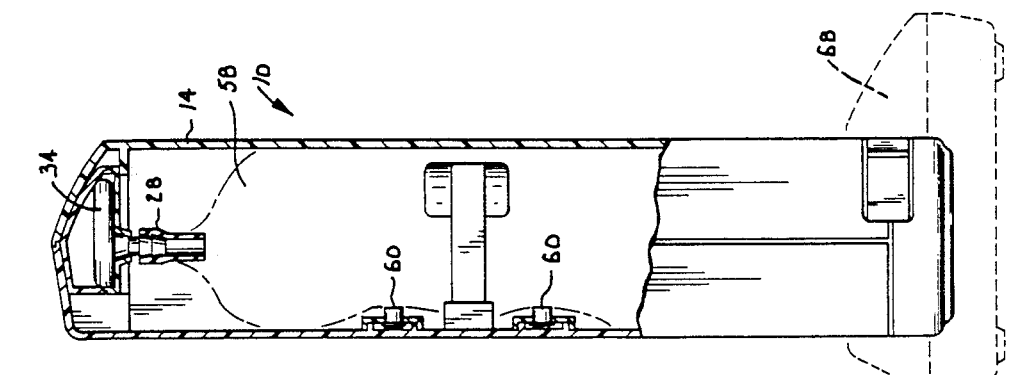
FIG. 2 is side elevational view of the urine collecting and storage device taken along line 2—2 of FIG. 1 with the charging stand shown in broken lines and portions of the device broken away to show internal details.
Figure 1:
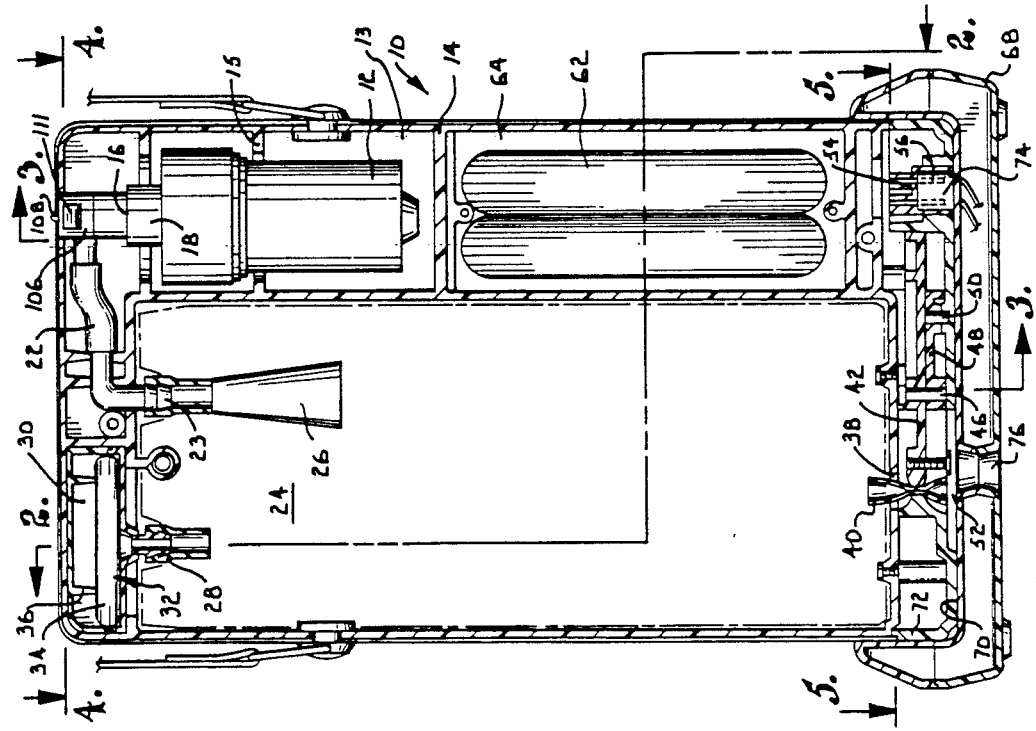
FIG. 1 is a rear sectional view of the urine collecting and storage device of the present invention positioned in a charging stand.

Referring now to the drawings in general and FIGS. 1-6 in particular, the collecting and storage device of the present invention is represented broadly by the numeral 10. The device 10 includes a centrifugal vane-type pump 12 which is contained in a pump compartment 13 within a housing 14. The pump 12 is supported in the compartment by baffles 15. The housing 14 and compartment 13 may be formed from blow-molded plastics or formed from other suitable material using well-known manufacturing techniques. The pump 12 has an inlet port 16 located at a top portion 18 and is positioned adjacent to a discharge port 20. A discharge line 22 leads from the discharge port and has an end 23 which extends into a urine storage chamber 24 located adjacent to the pump 12. The storage chamber 24 is preferably sized to hold a quantity of urine which would normally be excreted over a 24-hour period. A one-way duck bill valve 26 is coupled with the end 23 of the discharge line 22 to prevent flow of urine from the storage chamber 24 through the discharge line 22 should the device 10 be tipped over.

A port 28 is formed at the top of the storage chamber 24 and leads to a chamber 30 containing an air valve 32 which allows the venting of air from the storage chamber 24 but prevents the flow of urine through the valve 32. The air valve 32 comprises a pillow 34 containing a foam pad or other filler material and a deodorant specific to urine odor. The pillow 34 is maintained in place by baffles 36 and has a spun polypropylene covering which is air permeable but liquid impermeable. The housing 14 contains a series of narrow slits (not shown) adjacent the air valve chamber 30 to permit the venting of air through the housing 14.

A urine discharge port 38 is located at the bottom of the urine storage chamber 24 and includes a resilient tube 40 extending through the port 38. An L-shaped pinch lever 42 is pivotably mounted in a compartment 44 located beneath the urine storage chamber 24 and forms part of an overcenter mechanism to pinch closed the resilient tube 40. The lever 42 is pivotably coupled by a post 46 to a plate 48 which is pivotably coupled with a fixed pin 50. An opening 52 is formed in the bottom of the housing 14 in alignment with the discharge port 38 to allow the drainage of urine from the storage chamber 24. A male electrical plug 54 with protruding electrical contacts 56 is also coupled with the housing 14 at the bottom of the device 10.

A disposable liquid impermeable bag 58 may be placed within the urine storage chamber 24 to store the collected urine. The bag 58 is sized to fit within the urine storage chamber 24 and has suitable adapters for coupling with the urine discharge line 22, air port 28 and urine discharge port 38. Pressure switches 60 for indicating the liquid level in the bag 58 are coupled with the interior of the housing 14 in the storage chamber 24.

A pair of 7.2 volt Nicad batteries 62 comprise a self-contained power source and are located within a chamber 64 molded into the housing 14 and located beneath the pump chamber 13 and beside the storage chamber 24. The batteries are coupled with the electrical plug 54 and a printed circuit board 66 comprising standard electrical components which control the electrical functions of the device 10. The device 10 may be coupled with a charging unit 68 to charge the batteries and allow the device to be run by an external power source. The charging unit 68 includes a recessed area 70 for receiving a bottom portion 72 of the device 10 to support the device. A female electrical plug 74 is contained within the recessed area 70 for connection with the male plug 54 coupled with the bottom of the unit 10. The charging unit 68 is coupled with an external 110 volt AC power source and a transformer (not shown) is contained in the charging unit 68 to convert the power to 12 volts DC. The recessed area 70 also includes a drain hole 76.

Referring now to FIGS. 8 and 9, one embodiment of a male urine collecting vessel 78 will be described. The collecting vessel 78 comprises injection molded pliable material formed into an open-ended cup shape with a wide opening 80 at a top lip 82 and tapering to a smaller opening 84 at a bottom portion 86. The vessel 78 has an inner diameter of approximately $1\frac{3}{4}''$ and ribs 88 are formed in the interior of the vessel and extend from the lip 82 to the bottom portion 86. The size and shape of the vessel 78 may be varied to substantially conform to the size and shape of various individuals. A sanitary, liquid impermeable liner 89 which is open at both ends and shaped to fit within the vessel 78 and fit loosely over the individual 90 is disposed within the vessel 78 and draped over the lip 82. The liner 89 may be formed from unwoven fabric such as spun polypropylene which may be heat dot sealed for greater strength. A funnel shaped insert 91 is molded into the bottom portion 86 and includes electrical sensors 92 and a barb fitting 94 for a 3/16" I.D. tubing 96. The tubing 96 includes electrical wires 98 encased in plastic which are coupled with the electrical sensors 92 to form a liquid sensing circuit. Referring now to FIG. 7, the other end of the tubing 96 is coupled with a quick connect plug 100 with an extending liquid connector 102 and recessed female electrical contacts 104. A grooved ring 105 is formed in the liquid connector 102. The plug 100 may be connected with a mating quick connect plug 106 which is coupled with the pump inlet port 16. The plug 106 has projecting male electrical contacts 108 and an opening 110 for receiving the liquid connector 102. A locking lever 111 is provided for engaging the grooved ring 105 to prevent accidental disengagement of the plugs 100 and 106.

Referring now to FIG. 10, a disposable garmet which may be used to maintain the urine collecting vessel 78 in place is designated by the numeral 112. The garmet 112 comprises a waist strap 114 and leg straps 116 coupled with a pouch 118 having a bottom opening 120. The collecting vessel 78 is supported in the pouch 118 with the tubing 96 extending through the opening 120. Pressure sensitive tape 122 is coupled with the straps 114 and 116 for fastening the straps when wrapped around the waist and upper portions of the leg, respectively.

In use, a disposable liner 89 is inserted into the collecting vessel 78 and folded over the lip 82 of the vessel. The vessel 78 is then inserted into the pouch 118 of the disposable garmet 112 with the bottom portion 86 of the vessel and the tubing 96 threaded through the pouch opening 120. The garmet 112 is then placed on the male patient and the waist strap wrapped around the patient's waist and fastened with the tape 122. The vessel is then properly positioned in relation to the genital area and the leg straps 116 are then wrapped around the patient's legs, slipped through the waist strap 114 and fastened with the pressure tape. The patient or individual may then slip on outer clothing with the end of the tubing 96 containing the plug 100 placed in an accessable position for connection with the mating plug 106 so that a continuous internal passageway is formed from the vessel 78 to the pump 12 contained in the housing 14. The liquid sensing circuit is also activated when the plugs are connected. The device 10 is then removed from the charging unit 68 and carried by the patient to allow mobility of the patient. The device 10 may be discretely carried by a shoulder strap and concealed under clothing to allow the individual to engage in normal activities. For those patients who are bedridden, the device 10 is simply left in its charging unit 68.

In operation, any urine in the collecting vessel 78 is funneled by the liquid impermeable liner 80 away from the individual to the funnel shaped insert 91 where it contacts the electrical sensors 92. The sensors 92 operate on 5 volts with a current of 0.000040 amps. The liquid sensing circuit is normally open and closes when the urine contacts the sensors 92. The pump 12 is automatically activated by the closing of the circuit and creates a vacuum which draws air and urine through the tubing 96 and inlet port 16. The ribs 88 on the interior of the vessel 78 ensure that air is drawn though the opening 80 at the lip 82 and prevents the vessel from collapsing on the individual. The pump continues to draw urine from the vessel 78 until the liquid sensing circuit opens after the urine is removed. A timer may also be incorporated into the liquid sensing circuit to continue operation of the pump for a period of time after the circuit opens to draw air through the vessel to ensure complete drying. Unless the individual is in a prone position, the vessel 78 is preferably loosely worn to limit contact with the skin of the individual. When the individual is in a prone position, the lip 82 and liner 80 are positioned more securely against the genital region to prevent leakage of urine form the vessel 78 while allowing for the flow of air through the vessel 78. The liner 89 provides a sanitary lining which may be regularly changed and ensures that the urine is funneled away from the skin of the individual.

The air and urine are drawn through the pump 12 and routed through the discharge line 22 into the storage chamber 24. The urine collects in the bag 58 and the air exits through the air port 28 and air valve 32 where the deodorant contained in the pillow 34 masks any urine odor. As the bag 58 fills with urine over a period of time, the pressure switches are depressed when the urine level reaches predetermined levels. The switches may be coupled with an audible or visual alarm which will alert the individual to empty the bag 58. The bag may be conveniently emptied into a suitable receptacle by moving the pinch lever 42 to the released position as shown in FIG. 6 to allow the urine to drain through tube 40 and opening 52. When the bag is drained the lever 42 is simply returned to the closed position as shown in FIG. 5 with the lever 42 pinching the tube 40 to seal the discharge port 38.

Referring now to FIG. 11 a different embodiment of a male collecting vessel 124 is shown. The vessel 124 is constructed of similar materials as vessel 78 and is shaped for use by a highly retracted male or a male in a prone position. A lip 126 of the vessel 124 flares outwardly and provides a surface on which a circular lip ring 128 is coupled. The ring 128 may be formed from a foam pad or other air permeable substances. A liquid impermeable and air permeable liner 130 of similar material as liner 89 is disposed within the vessel 124 and drapped over the lip ring 128. The vessel 124 has a bottom portion 132 and an insert (not shown) coupled with tubing 134. These elements are similar in construction as the respective elements described with respect to vessel 78 and will not be detailed here.

In use, the vessel 124 is securely positioned at the genital region of a retracted or prone male using a garmet such as shown in FIG. 10 and previously described. The liquid impermeable liner 130 and lip ring 128 seal against the individual to present a barrier to the flow of urine. When the presence of urine in the vessel 124 is detected by the sensors (not shown), the pump is activated in the same fashion as has been previously described to draw air and urine from the vessel 124 until the vessel is dry. The air permeable liner 130 and lip ring 128 ensure that the air is available to the vessel 124 and prevent collapse of the vessel. The liner 130 also directs urine away from the individual and funnels it toward the bottom portion 132.

Referring now to FIG. 12, an embodiment of a collecting vessel which may be utilized by females is represented by the numeral 136. The vessel 136 comprises an elongated collecting cup 138 formed from injection molded pliable material and having a wide opening 140 and an outwardly extending peripheral lip 142 at the opening 140. Tubing 144, identical with tubing 96 and 134 previously described, is coupled with an opening (not shown) provided at a bottom end 146 of the cup 138 for removal of the urine. Liquid sensors (not shown) as previously described with respect to the male collecting vessels are located at the juncture of the tubing 144 and the cup 138. A flow-through membrane 148 is positioned on lip 142 and is sized to cover the opening 140. The membrane 148 may be formed from non-woven plastic and is highly permeable but has a very low absorption rate to allow urine to quickly pass through to the collecting cup 138. A soft open-cell foam pad 150 with a centrally open portion 152 conforming to opening 140 is positioned between membrane 148 and a liquid impervious cover 154. The cover 154 also has an open portion 156 and includes a portion 158 which allows the cover 154 to be coupled with the collecting cup 138. The cover 154 is constructed from relatively liquid impermeable but highly air permeable, unwoven fabric of spun polypropylene.

The female collecting vessel 136 serves the same function as the male collecting vessels 78 and 124. The female vessel is securely positioned to the female genital area using a suitable garmet which may be similar to that shown in FIG. 10. The presence of urine in the collecting cup 138 is detected by the liquid sensors (not shown) and the pump 12 is then activated to draw air and urine from the collecting vessel 136. The individual is separated from contact with the collecting cup 138 by the cover 154, pad 150 and membrane 148 for hygienic and comfort purposes. The air permeable pad and cover ensure that air is available to the collecting vessel 136 to prevent the vessel from adhering by suction to the skin of the individual and at the same time prevent leakage of urine from the vessel 136. The cover 154, pad 150 and membrane 148 may routinely be replaced for hygienic purposes.

Another embodiment of a female urine collecting vessel 160 is shown in FIG. 13. The vessel 160 is constructed from the same materials used with the vessel 136 previously described. The vessel 160 has a urine collecting cup 162 identical to cup 138, a flow-through membrane 164 and an open-celled foam pad 166 covered with a liquid impermeable and air permeable cover 167. The vessel 160 also includes a semi-rigid foam dam 168 positioned on top of the foam pad 166 at a bottom edge 170 of the vessel. The foam dam 168 is shaped to fit tightly against a female's genital region to prevent urine from escaping from the vessel. Liquid sensors (not shown) are contained in the tubing 172 near the juncture with the collecting cup 162 and the use and operation of the cup is the same as previously described.

A still further embodiment of a female urine collecting vessel 174 is shown in FIGS. 14 and 15. The vessel 174 has a deeper well in a collecting cup 175 and is designed for use by females when in a prone or reclined position. The vessel 174 has an upwardly extending ridge 176 formed around opening 178 at an outwardly extending lip 180. The ridge 176 includes a dam portion 182 located at a bottom end 184 of the opening 178. The ridge 176 and dam 182 are designed to seal a foam pad (not shown) similar to pad 162 against the body of the individual to prevent the leakage of urine from the vessel 174. A flow through membrane and a liquid impermeable and air permeably cover may also be used in the same fashion previously described.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A device for use by an individual which removes urine from a genital region of the individual and stores the urine, said device comprising a collecting vessel shaped for external placement at the genital region to catch discharged urine within the vessel, storage means for temporarily storing the urine for subsequent disposal, conduit means connecting the collecting vessel and storage means, and pump means coupled with the conduit means for removing urine from the collecting vessel and transferring it through the conduit means to the storage means, said collecting vessel being shaped to substantially conform to the genital region and including an air permeable and substantially liquid impermeable liner within the vessel for directing urine to the conduit means and away from the individual and for separating the individual from the vessel.

2. The invention of claim 1, wherein the collecting vessel includes interior ribs to allow air to be drawn through the collecting vessel when the pump means draws urine from the vessel.

3. A method for removing urine from a genital region of an individual and temporarily storing the urine, said method comprising the steps of positioning a urine collection vessel at the genital region with a supporting garment, said vessel substantial·conforming to the genital region, coupling the vessel to a pump and a storage chamber, activating the pump when urine is present in the collecting vessel to remove the urine to the storage chamber, and lining the urine collection vessel with an air permeable and substantially liquid impermeable liner prior to positioning the vessel at the genital region to separate the individual from the vessel and to direct urine away from the individual.

4. The method of claim 3, including the steps of:
   detecting the presence of urine in the collecting vessel using liquid sensing means located within the vessel; and
   automatically activating the pump when the urine is detected.

5. The method of claim 3, including the step of inserting an air permeable pad at a lip of the vessel to allow the flow of air through the vessel when the pump is activated to remove the urine to the storage chamber.

6. In a device for use by an individual which removes urine from a genital region of the individual and stores the urine, said device including a collecting vessel shaped for external placement at the genital region to catch discharged urine within the vessel, storage means for temporarily storing the urine for subsequent disposal, conduit means connecting the collecting vessel and storage means, and pump means coupled with the conduit means for removing urine from the collecting vessel and transferring it through the conduit means to the storage means, wherein the improvement comprises,
   an air vent port in communication with said storage means to permit the release of air from the storage means as the air is replaced with the urine, said vent port including a foam pad with a deodorant specific to urine and a covering over the foam pad which is air permeable and liquid impermeable to permit the escape of air but prevent the escape of urine from the storage means.

7. The device of claim 6 wherein the covering is spun polypropylene.

* * * * *